(12) United States Patent
Slayton

(10) Patent No.: US 12,239,854 B2
(45) Date of Patent: *Mar. 4, 2025

(54) METHODS AND SYSTEMS FOR REMOVAL OF A TARGETED TISSUE FROM THE BODY

(71) Applicant: Guided Therapy Systems, LLC, Scottsdale, AZ (US)

(72) Inventor: Michael H. Slayton, Phoenix, AZ (US)

(73) Assignee: Guided Therapy Systems, LLC, Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/232,404

(22) Filed: Apr. 16, 2021

(65) Prior Publication Data

US 2022/0080226 A1 Mar. 17, 2022

Related U.S. Application Data

(63) Continuation of application No. 15/001,712, filed on Jan. 20, 2016, now abandoned.

(60) Provisional application No. 62/105,512, filed on Jan. 20, 2015.

(51) Int. Cl.
*A61N 7/02* (2006.01)
*A61N 7/00* (2006.01)

(52) U.S. Cl.
CPC ............. *A61N 7/02* (2013.01); *A61N 7/00* (2013.01); *A61N 2007/0034* (2013.01); *A61N 2007/025* (2013.01)

(58) Field of Classification Search
CPC .... A61N 7/02; A61N 7/00; A61N 2007/0034; A61N 2007/025; A61N 2007/0008; A61B 17/320068; A61B 2018/00458
See application file for complete search history.

(56) References Cited

U.S. PATENT DOCUMENTS

| | | | | |
|---|---|---|---|---|
| 6,488,626 | B1 * | 12/2002 | Lizzi | G01S 7/52042 601/3 |
| 2007/0106157 | A1 * | 5/2007 | Kaczkowski | A61B 8/587 600/438 |
| 2011/0251528 | A1 * | 10/2011 | Canney | A61N 7/02 601/3 |
| 2012/0143056 | A1 * | 6/2012 | Slayton | A61B 8/13 601/2 |

* cited by examiner

*Primary Examiner* — Hien N Nguyen
(74) *Attorney, Agent, or Firm* — GTC Law Group

(57) ABSTRACT

Methods and systems for acoustic treatment of tissue are provided. Acoustic energy, for example ultrasound energy, under proper functional control can penetrate deeply and be controlled precisely in tissue. Some aspects provide a method configured for removal of at least a portion of targeted tissue, such as a scar, abscess, non-cancerous tumor, or fibrous knot, in a tissue of the body.

18 Claims, 6 Drawing Sheets

METHODS AND SYSTEMS FOR REMOVAL OF A TARGETED TISSUE FROM THE BODY

CROSS-REFERENCE TO RELATED APPLICATIONS

This application is a continuation of U.S. patent application Ser. No. 15/001,712, filed Jan. 20, 2016, which is based on, claims priority to, and incorporates herein by reference U.S. Provisional Patent Application Ser. No. 62/105,512, filed Jan. 20, 2015.

BACKGROUND

Current methods for the removal of a targeted tissue from the skin or a tissue in a patient are varied and have mixed results. A targeted tissue embedded in the skin may be cut out, but will often be painful and leave a scar. Ultrasound methods have attempted to use shock waves, but they are limited to certain types of targeted tissues and damage the surrounding tissue. Likewise the technique of ablation is limited to only certain types of target tissues. Accordingly, it would be useful to develop new techniques for removing a targeted tissue in a tissue of the body of a patient with fewer side-effects and limitations of specific technologies to specific tissues.

SUMMARY

The present disclosure overcomes the aforementioned drawbacks by presenting a method for removal of targeted tissue from the body which utilizes acoustic energy treatment.

This disclosure provides a method for acoustic treatment of tissues for removal of targeted tissue which can be non-invasive. The method can include directing acoustic energy deposition into a tissue by creating an energy distribution function. The energy distribution function can be tuned to control treatment of a target zone within a tissue, targeted tissue embedded in the tissue, or any combination thereof to remove a targeted tissue or portion thereof. Examples of a targeted tissue are, but are not limited to, a hypertrophic scar, a keloidal scar, an abscess, a cancerous or non-cancerous tumor, a fibrous knot, or combinations thereof, in a body.

In one aspect, this disclosure provides a method of removing targeted tissue by inducing an acousto-mechanical or acousto-elastic effect in the targeted tissue embedded in a medium. The method can include one or more of the following steps: coupling an ultrasound energy source to the targeted tissue; and directing a pulsed first ultrasound energy from the ultrasound energy source into the targeted tissue, thereby initiating an acousto-mechanical or acousto-elastic effect in the targeted tissue. The ultrasound energy source can be configured to produce a pulsed first ultrasound energy having a frequency of between 100 kHz and 200 MHz and a pulse duration of between 1 ps and 1 ms. The ultrasound energy source can be configured to produce a pulsed first ultrasound energy having a frequency of between 100 kHz and 200 MHz, a pulse duration of between 1 ps and 1 ms, and a power of between 1 kW and 50 kW. The pulsed first ultrasound energy can have a pulse energy from 500 nJ to 5 J. The acousto-mechanical or acousto-elastic effect in the targeted tissue can exceed a fragmentation threshold of the targeted tissue.

In another aspect, this disclosure provides a method of removing a targeted tissue by treating the targeted tissue or a portion thereof in a body. The method can include one or more of the following steps: coupling an ultrasound energy source to the targeted tissue embedded in a tissue; and initiating, using a single ultrasound energy pulse from the ultrasound energy source, an acousto-mechanical or acousto-elastic effect in the targeted tissue that exceeds a fragmentation threshold of the targeted tissue and can fragment the targeted tissue or a portion thereof into a plurality of sub-particles of a size that can initiate an immune response which can remove the sub-particles, thereby removing the targeted tissue or a portion thereof.

In yet another aspect, this disclosure provides an ultrasound treatment system for removal of a targeted tissue, a portion thereof, or sub-particles thereof in a body. The ultrasound treatment system can include an ultrasound source and a control system. The ultrasound source can be configured to emit a propagating ultrasound energy having a propagating ultrasound pulse duration between 100 ps and 1 ms, a propagating ultrasound pulse power ranging from 1 kW to 50 kW, and a propagating ultrasound frequency between 100 kHz and 200 MHz. The control system can be configured to direct the ultrasound energy source to emit the propagating ultrasound energy to a target zone within the tissue containing a targeted tissue at an intensity gain between 500 and 25,000, thereby initiating an acousto-mechanical or acousto-elastic effect within the target zone. The acousto-mechanical or acousto-elastic effect can move the targeted tissue, a portion thereof, or sub-particles thereof. The targeted tissue, a portion thereof, or sub-particles thereof can be moved toward the surface of the tissue, expelling them from the tissue, or moved deeper into the tissue, to be absorbed by the body or removed by the immune system.

BRIEF DESCRIPTIONS OF THE DRAWINGS

DETAILED DESCRIPTION

Figure 1:
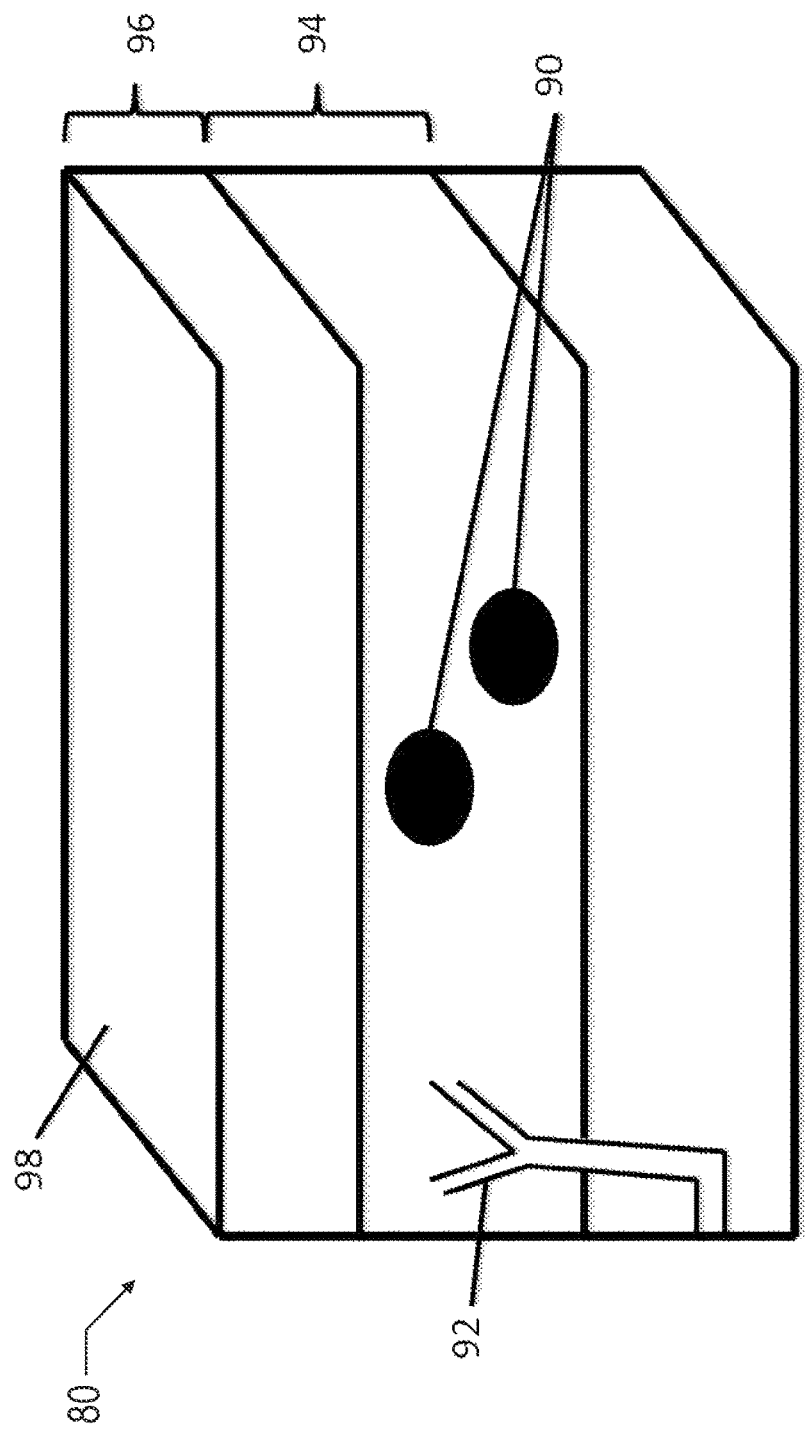
FIG. 1 is a cross-sectional view of layers of tissues, illustrating the placement of a targeted tissue.

Before the present invention is described in further detail, it is to be understood that the invention is not limited to the particular embodiments described. It is also understood that the terminology used herein is for the purpose of describing particular embodiments only, and is not intended to be limiting. The scope of the present invention will be limited only by the claims. As used herein, the singular forms "a", "an", and "the" include plural embodiments unless the context clearly dictates otherwise.

Specific structures, devices and methods relating to ultrasound treatment and operation for the removal of a targeted tissue from a tissue of the body are disclosed. It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements. When two or more ranges for a particular value are recited, this disclosure contemplates all combinations of the upper and lower bounds of those ranges that are not explicitly recited. For example, recitation of a value of between 1 and 10 or between 2 and 9 also contemplates a value of between 1 and 9 or between 2 and 10.

The various embodiments may be described herein in terms of various functional components and processing steps. It should be appreciated that such components and steps may be realized by any number of hardware components configured to perform the specified functions. For example, various embodiments may employ various cosmetic enhancement devices, visual imaging and display devices, input terminals and the like, which may carry out a variety of functions under the control of one or more control systems or other control devices. In addition, the embodiments may be practiced in any number of medical, non-medical, or cosmetic contexts and the various embodiments relating to a method and system for acoustic tissue treatment for removal of a targeted tissue from a tissue as described herein are merely indicative of some examples of the application for use in medical treatment or cosmetic enhancement. For example, the principles, features, and methods discussed may be applied to any medical, non-medical, or cosmetic application. Further, various aspects of the various embodiments may be suitably applied to medical, non-medical, or cosmetic applications for the skin, subcutaneous layers, or combinations thereof.

As used herein, the term "cosmetic enhancement" can refer to procedures, which are not medically necessary and are used to improve or change the appearance of a portion of the body. Since it is not medically indicated for improving one's physical well-being, cosmetic enhancement does not diagnose, prevent, treat, or cure a disease or other medical condition. Furthermore, cosmetic enhancement is not a method for treatment of the human or animal body by surgery or therapy nor a diagnostic method practiced on the human or animal body. Cosmetic enhancement is a non-surgical and non-invasive procedure. In some aspects, cosmetic enhancement can be a non-surgical and non-invasive procedure that is performed at home by a user who is not a medical professional.

As used herein, the term "lesion" shall refer to a void, a lesion, or a combination thereof, unless the context clearly dictates otherwise.

As used herein, the term "targeted tissue" shall refer to, but is not limited to, a hypertrophic scar, a keloidal scar, an abscess, a non-cancerous tumor, cancerous lesions, conglomeration of melanin, a fibrous knot, or combinations thereof, in a body or tissue. Other examples of the targeted tissue can include, but are limited to, scar tissue, melanocyte or melanin (hyperpigmentation), sebaceous gland, hair, a piece of cartilage, a tumor (either cancerous or benign), a fat cell, a muscle, and combinations thereof.

As used herein, the term "tissue" may refer to, but is not limited to, at least one of an epidermal layer, a dermal layer, a fat layer, a muscle layer, a subcutaneous tissue, or combinations thereof, in a body.

As used herein, the term "fragmentation" shall refer to any pressure- or temperature-induced expansion within a material that breaks apart the material, including a microexplosion, a fragmentation, or a combination thereof, unless the context clearly dictates otherwise.

As used herein, the term "fragmentation threshold" shall refer to the minimum amount of energy directed at an object in a region of interest which causes the object to fragment. Fragmentation can be the result of an acousto-mechanical effect which rapidly increases pressure, an acousto-elastic effect which rapidly increases temperature, or a combination thereof.

This disclosure provides systems and methods for removal of a targeted tissue from a body or tissue which utilizes acoustic energy treatment of tissue.

Referring to FIG. 1, a cross-sectional view of layers of tissue in a body, illustrating a schematic of an embedded targeted tissue. A targeted tissue 90 of a size which cannot be up-taken by immune cells or transported to lymphatic channels 92 for clearance, are present in a tissue 80.

Figure 2:
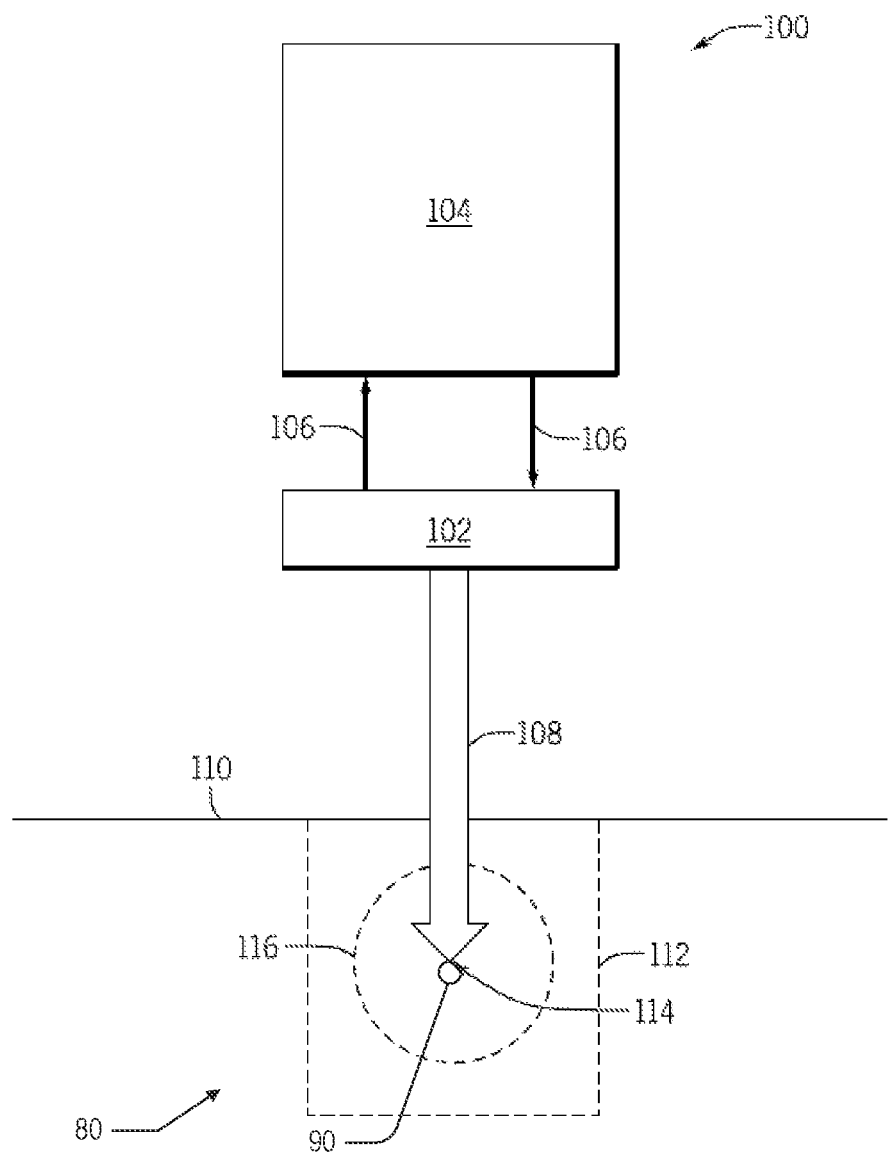
FIG. 2 is a block diagram illustrating an exemplary ultrasound delivery system, according to one aspect of the present disclosure.

Referring to FIG. 2, this disclosure provides an ultrasound delivery system 100. The ultrasound delivery system can include an ultrasound energy source 102 and a control system 104, which can be electronically coupled to one another via one or more communication conduits 106. The one or more communication conduits 106 can be wired or wireless. The ultrasound energy source 102 can be configured to emit propagating ultrasound energy 108. The control system 104 can be configured to direct the ultrasound energy source 102 to emit propagating ultrasound energy 108.

Still referring to FIG. 2, this disclosure provides systems and methods where the ultrasound energy source 102 can transmit ultrasound energy 108 across an optional boundary 110, such as a surface, and into a region of interest ("ROI") 112. The propagating ultrasound energy 108 can be delivered to a target zone 114 within the ROI 112 containing at least part of a targeted tissue 90. The propagating ultrasound energy 108 can create an acoustic energy field 116 within the ROI 112. The ROI 112 can include a medium, as described herein.

In certain aspects, the ultrasound energy source 102 can be positioned within an ultrasound probe. The ultrasound probe can optionally be handheld. The control system 104 can be located within the ultrasound probe or remote from the ultrasound probe.

Figure 3:
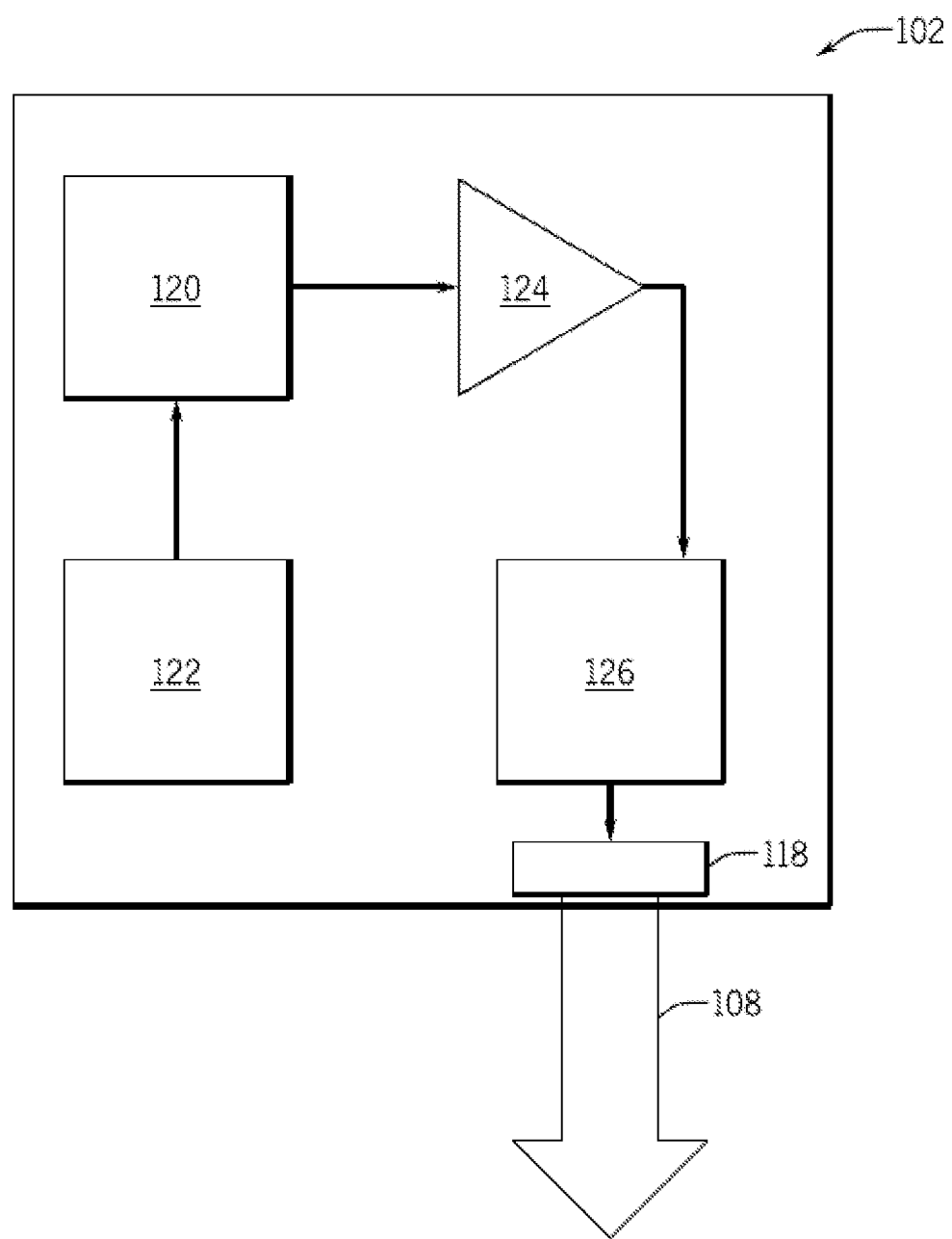
FIG. 3 is a block diagram of an exemplary ultrasound source, according to one aspect of the disclosure.

Referring to FIG. 3, the ultrasound energy source 102 can include a transducer 118, which is configured to emit propagating ultrasound energy 108. The ultrasound energy source can further include a function generator 120, which can be powered by a power supply 122. The function generator 120 can be a radiofrequency ("RF") generator, a frequency generator, a pulse generator, a waveform generator, or a combination thereof. The power supply 122 can be located within the ultrasound energy source 102 or remote from the ultrasound energy source 102. The function generator can provide a drive signal to the transducer 118 that initiates the emission of propagating ultrasound energy 108. The drive signal can have a drive frequency and a drive amplitude. The drive signal can be an RF signal. The ultrasound energy source 102 can optionally include an amplifier 124 that is configured to receive the drive signal, controllably amplify the drive signal to produce an amplified drive signal, and transmit the amplified drive signal to the transducer 118. The ultrasound energy source 102 can further optionally include an impedance matching network 126. The impedance matching network 126 can be configured to adjust the effective impedance or the load of the transducer 118 to match the impedance of the function generator 120 or the amplifier 124. The impedance matching network 126 can be configured to receive the drive signal from the function generator 120 and transmit a matched drive signal to the transducer 118 or to receive the amplified drive signal from the amplifier 124 and transmit a matched, amplified drive signal to the transducer 118.

In certain aspects, the propagating ultrasound energy 108 can be pulsed. The propagating ultrasound energy 108 can have a propagating ultrasound pulse duration ranging from 100 ps to 1 ms, including but not limited to, a propagating ultrasound pulse duration ranging from 100 ps to 1 μs, from 100 ps to 100 μs, from 500 ps to 500 ns, from 500 ps to 750 ns, from 1 ns to 10 μs, from 1 ns to 500 μs, from 200 ns to 1 ms, from 500 ns to 500 μs, from 1 us to 50 μs, from 1 us to 1 ms, or combinations of the lower and upper bounds of those ranges which are not explicitly set forth. The propagating ultrasound energy 108 can have a propagating ultrasound pulse power ranging from 1 kW to 50 kW, including but not limited to, a propagating ultrasound pulse power ranging from 1 kW to 5 kW, or from 1 kW to 10 kW. The propagating ultrasound energy 108 can have a propagating ultrasound pulse energy ranging from 500 nJ to 5 J, including but not limited to, a propagating ultrasound pulse energy ranging from 500 nJ to 2.5 mJ, from 500 nJ to 37.5 mJ, from 500 nJ to 100 mJ, from 500 nJ to 500 mJ, from 2000 to 5 J, from 500 μJ to 5 J, from 1 mJ to 250 mJ, from 1 mJ to 5 J, or combinations of the lower and upper bounds of those ranges which are not explicitly set forth. Ultrasound pulse durations described herein correspond to the duration of the ultrasound pulse itself and not the duration of a drive pulse or any other pulses related to the generation of ultrasound. Ultrasound pulse durations can be measured as a −6 dB pulse beam-width or a −3 dB pulse beam width.

In certain aspects, the propagating ultrasound energy 108 can have a specific frequency. The propagating ultrasound energy 108 can have a propagating ultrasound frequency ranging from 100 kHz to 200 MHz, including but not limited to, a propagating ultrasound frequency ranging from 500 kHz to 25 MHz, from 500 kHz to 200 MHz, from 1 MHz to 5 MHz, from 1 MHz to 7 MHz, from 1 MHz to 10 MHz, from 1 MHz to 20 MHz, from 1 MHz to 25 MHz, from 1 MHz to 30 MHz, from 1 MHz to 50 MHz, from 1 MHz to 200 MHz, from 2 MHz to 5 MHz, from 2 MHz to 10 MHz, from 2 MHz to 200 MHz, from 3 MHz to 7 MHz, or combinations of the lower and upper bounds of those ranges which are not explicitly set forth.

In certain aspects, the ultrasound energy source 102 can be configured to deliver propagating ultrasound energy 108 to the target zone 116 with an intensity gain relative to the intensity immediately after emission from the ultrasound energy source 102. The intensity gain can be in a range from 500 to 25,000, including but not limited to, a range from 1000 to 10,000. The intensity gain can be at least 500 or at least 1000.

In certain aspects, the ultrasound energy 108 can be configured to be delivered to various depths below a surface. For example, the ultrasound energy 108 can be configured to be delivered to a depth between 0.1 mm and 50 mm below a surface, including but not limited to, a depth between 0.2 mm and 2 mm, or a depth of at least 3 mm below the surface.

In certain aspects, the ultrasound delivery system 100 can further include an ultrasound imager configured to image at least a portion of the ROI 112. The ultrasound imager can be located within the ultrasound probe or remote from the ultrasound probe. The ultrasound imager can be used, but is not limited to, in determining the depth or size of a targeted tissue 90 within the tissue 80.

In certain aspects, the ultrasound delivery system 100 can further include a secondary ultrasound energy source configured to delivery a secondary propagating ultrasound energy to the ROI 112 or the targeted tissue 90 thereby establishing a secondary ultrasound energy field therein. A set of parameters for delivering the secondary ultrasound energy can include a secondary ultrasound frequency ranging from 100 kHz to 200 MHz, a secondary ultrasound power ranging from 1 kW to 10 kW, and a secondary ultrasound pulse duration ranging from 500 us to 10 s. Delivering secondary ultrasound energy under these conditions can initiate a thermal effect, a cavitation effect, or a combination thereof in the targeted tissue 90. For certain applications, the secondary ultrasound frequency can range from about 500 kHz to 25 MHz, from 500 kHz to 200 MHz, from 1 MHz to 5 MHz, from 1 MHz to 7 MHz, from 1 MHz to 10 MHz, from 1 MHz to 20 MHz, from 1 MHz to 25 MHz, from 1 MHz to 30 MHz, from 1 MHz to 200 MHz, from 2 MHz to 5 MHz, from 2 MHz to 10 MHz, from 2 MHz to 200 MHz, or combinations of the lower and upper bounds of those ranges which are not explicitly set forth. For certain applications, the secondary ultrasound power can range from 1 kW to 10 kW. For certain applications, the secondary pulse duration can range from 500 us to 1 ms, from 500 us to 10 ms, from 500 us to 100 ms, from 500 us to 1 s, from 1 ms to 50 ms, from 1 ms to 500 ms, from 1 ms to 1 s, from 1 ms to 10 s, from 50 ms to 100 ms, from 50 ms to 1 s, from 50 ms to 10 s, from 100 ms to 1 s, from 500 ms to 10 s, or from 1 s to 10 s, or combinations of the lower and upper bounds of those ranges which are not explicitly set forth.

In certain aspects, the ultrasound delivery system 100 can further include a secondary energy source configured to delivery a secondary energy to at least a portion of the ROI 112. The secondary energy source can be a photon-based energy source, an RF energy source, a microwave energy source, a plasma source, a magnetic resonance source, or a mechanical device capable of generating positive or negative pressures. Examples of a photon-based energy source include, but are not limited to, a laser, an intense pulsed light source, a light emitting diode, and the like. The secondary energy source can be located within the ultrasound probe or remote from the ultrasound probe. The secondary energy source can be configured to deliver the secondary energy before, during, or after the delivery of the propagating ultrasound energy 108. In certain aspects, the ultrasound delivery system 100 can further include an energy sink configured to remove energy from the ROI 112, for example, by providing a cooling effect the ROI 112.

Figure 4A:
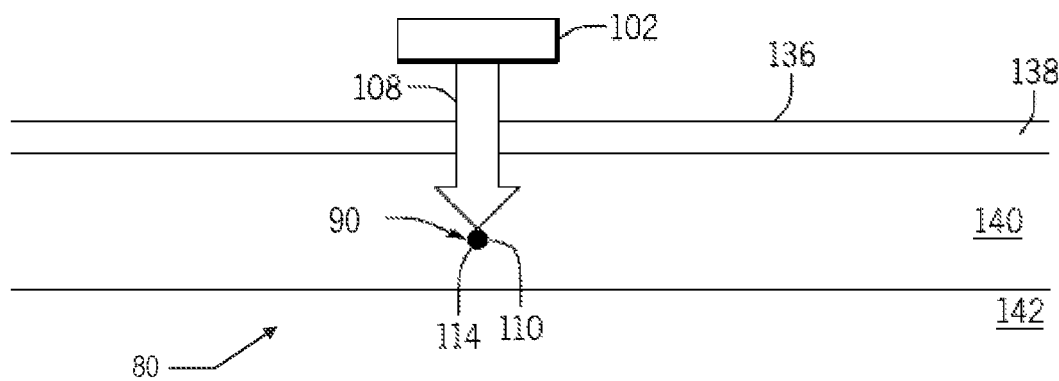
FIG. 4A is a cross-sectional view illustrating one stage of exemplary method, according to one aspect of the present disclosure.
Figure 4B:
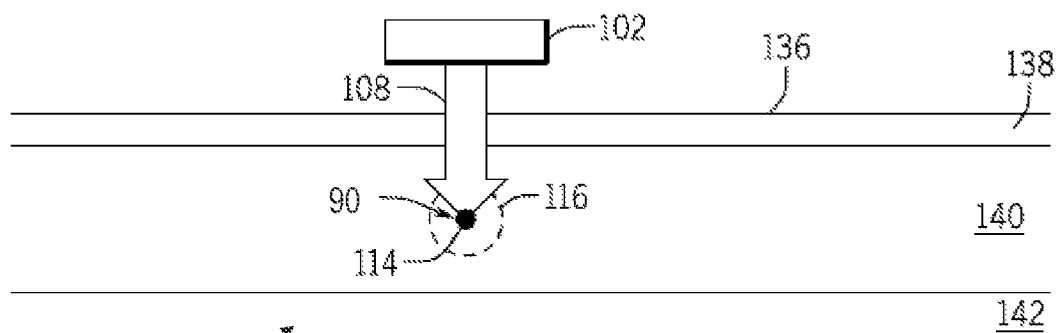
FIG. 4B is a cross-sectional view illustrating one stage of exemplary method, according to one aspect of the present disclosure.
Figure 4C:
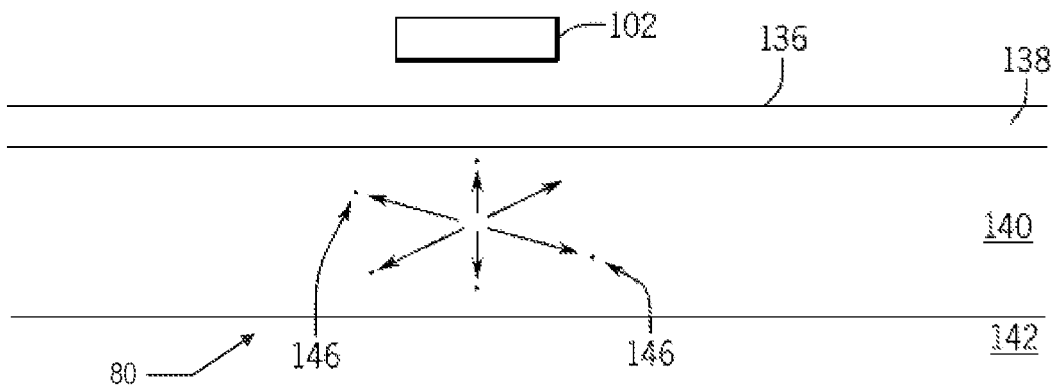
FIG. 4C is a cross-sectional view illustrating one stage of exemplary method, according to one aspect of the present disclosure.

Referring to FIGS. 4A, 4B, and 4C, a series of cross-sectional views are shown of an ultrasound energy source 102 directing propagation ultrasound energy 108 through a first medium layer surface 136, such as a skin surface 98, and a first medium layer 138, such as an epidermis layer 96, into a second medium layer 140, such as a dermis layer 94, but not into a third medium layer 142, such as a subcutaneous tissue layer, and the resulting effect. The propagating ultrasound energy 108 can be delivered into a targeted tissue 90 embedded in the first 138, second 140, or third medium layer 142.

Referring to FIG. 4A, the cross-sectional view is shown before an acoustic energy field 116 has been established within the targeted tissue 90 and surrounding portion of the second medium layer 140. A boundary 110, such as the outer surface of the targeted tissue, can separate the targeted tissue 90 from the second medium layer.

Referring to FIG. 4B, the cross sectional view is shown as the propagating ultrasound energy 108 passes through the boundary 110 and into the targeted tissue 90 to produce an acoustic energy field 116 in the targeted tissue 90 and surrounding portion of the second medium layer 140, which can generate a non-linear effect within the targeted tissue 90. In certain aspects, the non-linear effect can be an acousto-mechanical effect, an acousto-elastic effect, or a combination thereof in the targeted tissue 90.

Referring to FIG. 4C, the cross-sectional view is shown after the non-linear effect has caused a fragmentation in the targeted tissue 90, which can create a plurality of sub-particles 146. In certain aspects, the sub-particles 146 are of a size which renders them less visible than the targeted tissue 90 from the surface. In certain aspects, the sub-particles 146 are of a size which can be up-taken by immune cells and transported to the lymph system through lymphatic channels 92 for clearance. In certain aspects, an acoustic impedance of the targeted tissue 90 can be greater than an acoustic impedance of the second medium layer 140 and the boundary 110 can be the site of an acoustic impedance mismatch between the targeted tissue 90 and the second medium layer 140.

The targeted tissue 90 can have a diameter of between 10 nm and 500 μm, including but not limited to, a diameter of between 25 nm and 250 μm, between 50 nm and 100 μm, between 100 nm and 50 μm, between 250 nm and 10 μm, between 500 nm and 1 μm, or combinations of the lower and upper bounds of those ranged which are not explicitly set forth.

Figure 5:
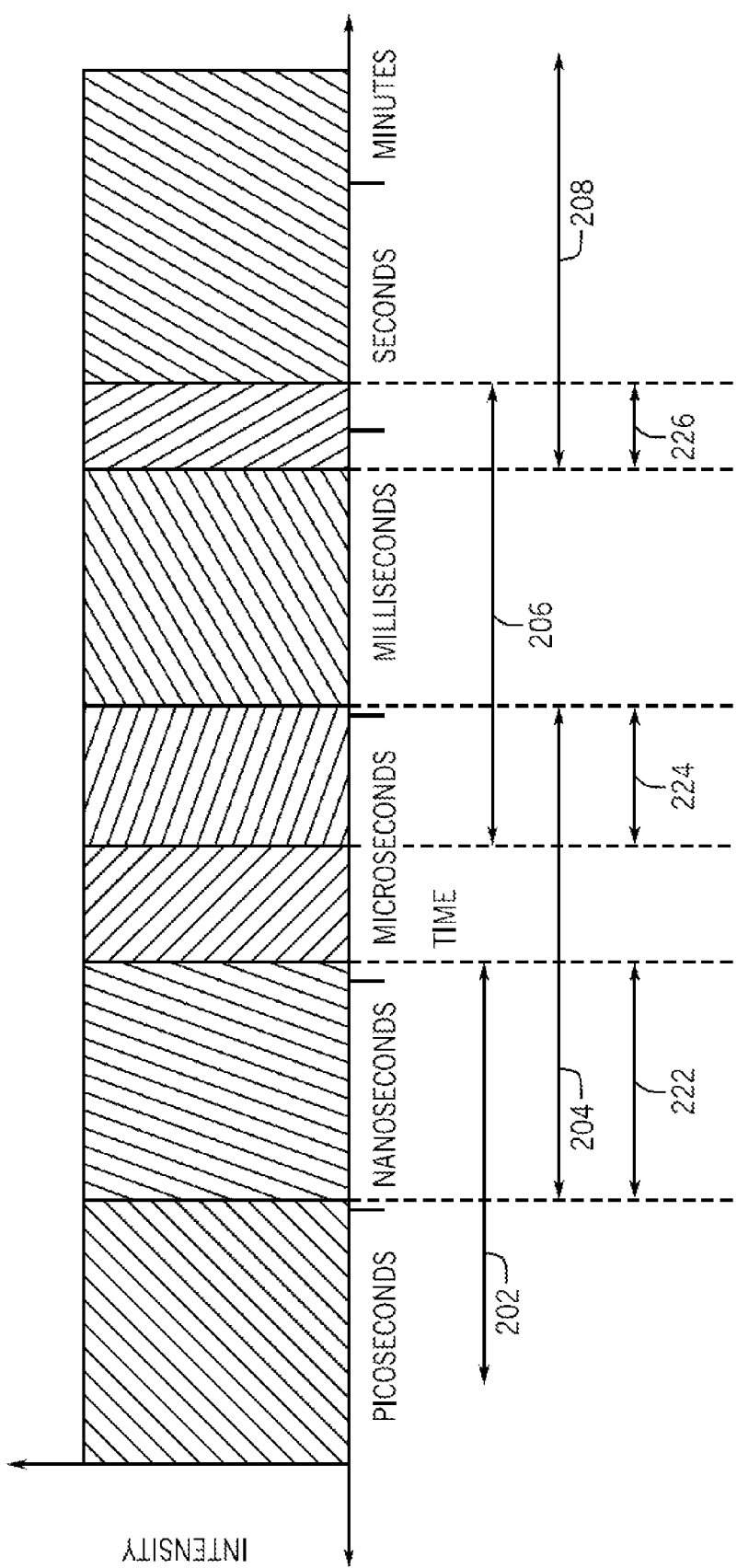
FIG. 5 is a graphical representation of the relationship between energy effects and acoustic pulse duration, according to one aspect of the present disclosure.

Referring to FIG. 5, a graphical representation 200, which has an x-axis 201 of ultrasound pulse duration represented as time and a y-axis 211 of ultrasound pulse intensity, illustrates the domains of various ultrasound sound energy initiated effects in a medium. Also as illustrated, some of the domains can overlap. These domains are approximations and the boundaries of the domain may shift for various reasons, such as changes in frequency, differences in the medium, or both. A person having ordinary skill in the art can calculate the effects of these changes using the equations described herein and equations known to those having ordinary skill in the art. These domains can be approximations in a frequency range of 1 MHz to 2 GHz. However, the frequency range can be narrower, for example, from 1 MHz to 30 MHz. In some applications, the frequency range can be from 1 MHz to 10 MHz, from 1 MHz to 7 MHz, or from 2 MHz to 5 MHz.

Still referring to FIG. 5, the first domain to be discussed is the domain of a thermal effect 208. The thermal effect raises the temperature of the medium by creating friction of molecules in the target zone of the medium from the oscillations of the acoustic energy. Different energy distribution fields can create one or more thermal effects in the medium. The energy distribution field can create a conformal elevated temperature distribution in the target zone of the medium. The ultrasound pulse duration for the domain of a thermal effect 208 is in a range from ms to minutes in a frequency range, as described above.

Still referring to FIG. 5, the second domain to be discussed is the domain of cavitation 206. At sufficiently high acoustic intensities, cavitation is the formation of microbubbles in a liquid portion of a medium. The interaction of the ultrasound field with the microbubbles can cause the microbubbles to oscillate in the medium (non-inertial cavitation or dynamic cavitation) or to grow and eventually implode (inertial cavitation). During inertial cavitation, very high temperatures inside the bubbles occur, and the collapse is associated with a shock wave that can mechanically damage the medium. However, the resulting damage to the medium is typically unpredictable. The ultrasound energy is unable to cause a cavitation effect in a solid medium because a truly solid medium does not contain any liquid, which is required for formation of microbubbles. The ultrasound pulse duration for the domain of cavitation 206 is in a range from ms to seconds in a frequency range, as described above. There is an overlap 226 of the domain of a thermal effect 208 and the domain of cavitation 206. In the overlap 226, both of the effects, the thermal effect and the cavitation effect can occur.

Still referring to FIG. 5, the third domain to be discussed is the domain of acousto-mechanical effect 204. The acousto-mechanical effect is a destruction of a target zone in a medium by overcoming the interaction energy of the molecules in the target zone with the ultrasound energy. For example, acousto-mechanical effect can overcome a heat capacity of a medium by mechanical means, which can dramatically increase pressure in the target zone from the inside out, thus resulting in a significant increase of temperature in the target zone. The pressure, P(r,t), generated at time t and position r by the acousto-mechanical effect can be described by the following equation:

$$\nabla^2 P(r,t) - \frac{1}{v^2}\frac{\partial^2 P(r,t)}{\partial t^2} = -\frac{\beta}{C_p}\frac{\partial h(r,t)}{\partial t} \qquad (1)$$

where β is the thermal expansion coefficient of the medium, v is the speed of sound in the medium, $C_p$ is the heat capacity of the medium, and h(r,t) is the heat generation per unit time and volume within the medium. The acousto-mechanical effect can cause a fragmentation in the target zone of the medium. The acousto-mechanical effect can cause an increase in a pressure in the target zone above a threshold of fragmentation of the medium in the target zone. A fragmentation pressure is a minimum pressure at which a substance (for example a targeted tissue) in the target zone of a particular medium (for example a tissue in a body) will explode (shatter, fragment). The ultrasound pulse duration for the domain of an acousto-mechanical effect 204 is in a range from ns to ms in a frequency range, as described above. There is an overlap 224 of the domain of cavitation 206 and the domain of an acousto-mechanical effect 204. In the overlap 224, both the cavitation and the acousto-mechanical effect can occur.

Still referring to FIG. 5, the fourth domain to be discussed is the domain of acousto-elastic effect 202. The acousto-elastic effect is an effect in a medium that arises from the combination of the pressure oscillations of an acoustic wave with the accompanying adiabatic temperature oscillations in the medium produced by the acoustic wave. Temperature of the surrounding medium is unchanged. The acousto-elastic effect is an effect in that can overcome threshold of elasticity of the molecules in the target zone of the medium. The acousto-elastic effect increases the temperature from the inside out by thermal diffusion, which can dramatically increase temperature in a target zone thus resulting in a raise in pressure in the target zone. The temperature, T(r,t), generated at time t and position r by the acousto-elastic effect can be described by the following equation:

$$\frac{\partial T(r,t)}{\partial t} - \alpha \nabla^2 T(r,t) = \frac{h(r,t)}{\rho C_p} \quad (2)$$

where α is the thermal diffusion coefficient of the medium and ρ is the density of the medium. The acousto-elastic effect can break the thermal elastic connection of the molecules in the target zone 114, which can cause a fragmentation in the target zone of the medium. The acousto-elastic effect can raise a temperature in the target zone above a fragmentation temperature of the medium in the target zone. A fragmentation temperature is a minimum temperature at which a substance (for example a targeted tissue) in the target zone of a particular medium (for example a tissue or layers of tissue in a body) will explode (shatter, fragment). The ultrasound pulse duration for the domain of an acousto-mechanical effect 202 is in a range from ps to ms in a frequency range, as described above. There is an overlap 222 of the domain of an acousto-mechanical effect 204 and the domain of acousto-elastic effect 202. In the overlap 222, both of the effects, the acousto-mechanical effect and the acousto-elastic effect can occur.

The acousto-mechanical effect causes a massive and rapid increase in pressure in a target zone of the medium. The acousto-elastic effect causes a massive and rapid increase of temperature in a target zone of the medium. The acousto-mechanical effect and the acousto-elastic effect are different than a photo-acoustic effect. A photo-acoustic effect is the conversion of light energy into acoustic energy. The acousto-mechanical effect and the acousto-elastic effect are different than a photo-mechanical effect. A photo-mechanical effect is the conversion of light energy into mechanical energy. Accordingly, an ultrasound source cannot initiate a photo-acoustic or photo-mechanical effect. In certain aspects, an acousto-mechanical or acousto-elastic effect can initiate a change in a state of matter of a material.

Spatial control of the acoustic energy field 116 can be achieved by spatial control of the propagating ultrasound energy 108 emission. One means of achieving spatial control of the propagating ultrasound energy 108 emission is through the configuration of the ultrasound energy source 102 by way of the control system 104. For example, spatial control can be achieved through one or more of the following: varying the placement of the acoustic energy source 102; varying the orientation of the acoustic energy source 102 in any of six degrees of freedom, including three translational degrees of freedom and three rotational degrees of freedom; varying environmental parameters, such as the temperature of an acoustic coupling interface; varying the coupling agent; varying the geometric configuration of the acoustic energy source 102; varying the number of transduction elements or electrodes in the ultrasound energy source 102; utilizing one or more lenses, variable focusing devices, stand-offs, transducer backing, or acoustic matching layers; and other spatial control processes known to one having ordinary skill in the ultrasound arts. Spatial control can be facilitated by open-loop or closed-loop feedback algorithms, for example, by monitoring a signal or effect and the spatial characteristics that produce the signal or effect in order to optimize the signal or effect. The propagating acoustic energy 108 can be focused to a minimum focal spot size that is wavelength dependent.

Temporal control of the acoustic energy field 116 can be achieved by temporal control of the propagating ultrasound energy 108 emission. One means of achieving temporal control of the propagating ultrasound energy 108 emission is through the configuration of the ultrasound energy source 102 by way of the control system 104. For example, temporal control can be achieved through one or more of the following: varying a drive amplitude; varying a drive frequency; varying a drive waveform; varying drive timing sequences; varying a pulse repetition rate; apodization of the propagating ultrasound energy 108 emission; other temporal control processes known to one having ordinary skill in the ultrasound arts. Temporal control can be facilitated by open-loop or closed-loop feedback algorithms, for example, by monitoring a signal or effect and the temporal characteristics that produce the signal or effect in order to optimize the signal or effect.

Using the equations and phenomena disclosed herein and other equations and phenomena known to a person having ordinary skill in the art of ultrasound treatment, a user can determine appropriate spatial and temporal parameters to provide to the control system 104, which can direct the ultrasound energy source 102 to generate a predictable propagating ultrasound energy 108 that causes a predictable acoustic energy field 116 within a material, such as a target medium (for example a tissue or layers of tissue in a body 94) or an object (for example a targeted tissue 90). The acoustic energy field 116 can be described by an acoustic energy function that can be mathematically determined by a person having ordinary skill in the art by using the equations and phenomena disclosed herein and other equations and phenomena known to a person having ordinary skill in the art of ultrasound treatment. The acoustic energy function can include three spatial dimensions and a time dimension.

The acoustic energy field 116 can result from an algebraic, geometric, convolved, or other mathematical combination of two or more acoustic energy fields 116 generated by one or more acoustic energy sources 102. The acoustic energy field 116 can correspond to a designed three-dimensional thermal energy distribution.

For certain applications, a set of parameters for delivering ultrasound energy can include an ultrasound frequency ranging from about 500 kHz to about 25 MHz, an ultrasound power ranging from about 1 kW to about 10 kW, an ultrasound pulse width ranging from about 500 ns to about 500 μs, and an ultrasound energy ranging from about 500 μJ to about 5 J. For certain applications, the ultrasound frequency can range from about 1 MHz to about 5 MHz. Delivering ultrasound energy under these conditions can initiate a non-linear effect in the target zone 114, such as creating a voxel of destruction in the target zone 114, initiating an acousto-mechanical effect in the target zone 114, initiating an acousto-elastic effect in the target zone 114, or a combination thereof.

For certain applications, a set of parameters for delivering ultrasound energy can include an ultrasound frequency ranging from about 1 MHz to about 10 MHz, an ultrasound power ranging from about 1 kW to about 5 kW, an ultrasound pulse width ranging from about 1 us to about 50 μs, and an ultrasound energy ranging from about 1 mJ to about 250 mJ. Delivering ultrasound energy under these conditions can initiate a non-linear effect in the target zone 114, such as initiating an acousto-mechanical effect in the target zone 114. In some aspects, Delivering ultrasound energy under these conditions can initiate a non-linear effect and a mechanical effect in the target zone 114, such as initiating an acousto-mechanical effect and a cavitation effect in the target zone 114.

For certain applications, a set of parameters for delivering ultrasound energy can include an ultrasound frequency ranging from about 2 MHz to about 200 MHz, an ultrasound power ranging from about 1 kW to about 5 kW, an ultrasound pulse width ranging from about 500 ps to about 500 ns, and an ultrasound energy ranging from about 500 nJ to about 2.5 mJ. For certain applications, the ultrasound frequency can range from about 2 MHz to about 5 MHz. Delivering ultrasound energy under these conditions can initiate a non-linear effect in the target zone 114, such as initiating an acousto-mechanical effect in the target zone 114, initiating an acousto-elastic effect in the target zone 114, or a combination thereof.

For certain applications, a set of parameters for delivering ultrasound energy can include an ultrasound frequency ranging from about 100 kHz to about 200 MHz, an ultrasound power ranging from about 1 kW to about 50 kW, an ultrasound pulse width ranging from about 500 ps to about 750 ns, and an ultrasound pulse width ranging from about 500 nJ to about 37.5 mJ. Delivering ultrasound energy under these conditions can initiate a non-linear effect in the target zone 114, such as initiating an acousto-mechanical effect in the target zone 114, initiating an acousto-elastic effect in the target zone 114, or a combination thereof.

For certain applications, a set of parameters for delivering ultrasound energy can include an ultrasound frequency ranging from about 2 MHz to about 10 MHz, an ultrasound power ranging from about 1 kW to about 5 kW, an ultrasound pulse width ranging from about 200 ns to about 1 ms, and an ultrasound energy ranging from about 200 µJ to about 5 J. Delivering ultrasound energy under these conditions can initiate a non-linear effect, such as an acousto-mechanical effect, in the target zone 114. Delivering ultrasound energy under these conditions can initiate a non-linear effect in the target zone 114, such as creating a voxel of destruction in the target zone 114, initiating an acousto-mechanical effect in the target zone 114, initiating an acousto-elastic effect in the target zone 114, or a combination thereof.

In certain aspects, any of the aforementioned sets of parameters can include a range disclosed elsewhere in this disclosure that fits within the range disclosed in the set of parameters. Depending on the desired effect, interleaving pulses can be utilized to alter the temporal parameters or 2 or more pulsed ultrasound energies can be utilized to alter the spatial parameters, the temporal parameters, or both.

In certain aspects, the acousto-mechanical effect or the acousto-elastic effect generated within an object (for example a targeted tissue) as described herein can be sufficient to overcome Young's Modulus of the medium. Overcoming Young's Modulus can cause the object to fragment, shatter, explode, or any combination thereof. Young's Modulus (E) can be calculated by the following equation:

$$E = \frac{\sigma}{\varepsilon} = \frac{FL_0}{A_0 \Delta L} \quad (3)$$

where σ is the tensile stress on an object, ε is the extensional strain on an object, F is the force exerted on an object, $A_0$ is the original cross-sectional area through which the force is applied, $L_0$ is the original length of the object, and ΔL is the amount by which the length of the object changes.

The ultrasound energy source 102 can be acoustically coupled, directly or indirectly, to the target zone 114, the ROI 112, the boundary 110, or any combination thereof by way of a coupling agent. In certain aspects, the acoustic coupling agent can be selected from the group consisting of water, acoustic coupling gel, other materials providing a desired transformation of acoustic impedance from the source to the target, and combinations thereof.

Figure 6:
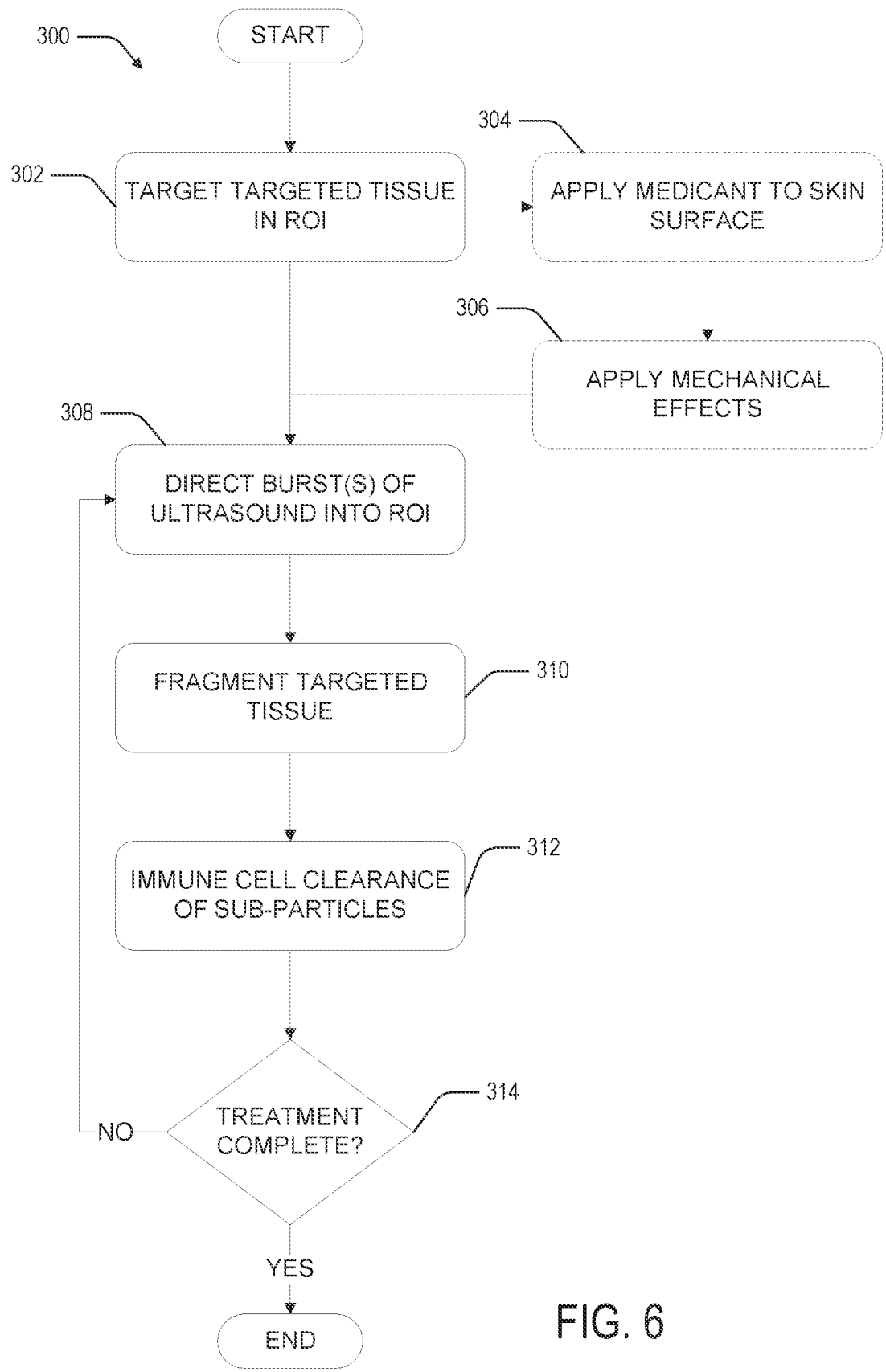
FIG. 6 is a flow chart of an exemplary method, according to one aspect of the present disclosure.

Referring to FIG. 6, a flow chart is shown of a method 300 for removing a targeted tissue 90 by creating an acousto-mechanical or acousto-elastic effect to fragment a targeted tissue 90, or portion thereof, into sub-particles 146. The sub-particles 146 can be less visible in the tissue than the targeted tissue. The sub-particles 146 can be of a size which can be up-taken by immune cells and transported to the lymph system through lymphatic channels 92 for clearance.

Still referring to FIG. 6, the method 300, at process block 302, can begin with targeting a targeted tissue 90 by, but not limited to, an ultrasound imager incorporated in the ultrasound delivery system, by determining the depth and size of the targeted tissue 90 within the tissue 80. In certain aspects, the method 300 can include targeting a boundary 110 between the targeted tissue 90 and the tissue 80. After targeting optional steps can be included in the method 300 including, but not limited to, applying a medicant (for example numbing agents or coupling ultrasound gels) to the skin surface 304 or mechanical effects can be applied 306.

Still referring to FIG. 6. the method 300, at process block 208, can include coupling an ultrasound energy source 102 to the targeted tissue 90 and directing a pulsed ultrasound energy 108 from the ultrasound energy source 102 into the targeted tissue 90. In certain aspects, the method 300 can include coupling the ultrasound energy source 102 to a boundary 110 between the targeted tissue 90 and the tissue 80 and directing the pulsed ultrasound energy 108 from the ultrasound energy source 102 into the boundary 110 between the targeted tissue 90 and the tissue 80. Directing the pulsed ultrasound energy 108 into the targeted tissue 90 can initiate an acousto-mechanical or acousto-elastic effect in the targeted tissue 90. The pulsed ultrasound energy 108 can have ultrasound properties as disclosed herein. The method 300 can include delivering a first energy, a second energy, a third energy, or an nth energy, simultaneously or with various time delays. The first, second, third, or nth energy can be an ultrasound energy or a secondary energy. The method 300 can include delivering a second ultrasound energy into the targeted tissue 90 prior to the delivery of the pulsed ultrasound energy. This second ultrasound energy can create or enhance an acoustic mismatch between the target zone or targeted tissue 90 and the surrounding tissue 80.

At process block 310 the acousto-mechanical or acousto-elastic effect generated by the method 300 can overcome a fragmentation threshold, thereby causing fragmentation within the targeted tissue 90 located in the target zone 114. In certain aspects, the fragmentation can generate sub-particles 146.

At process block 312 sub-particles of a certain size can be up-taken by immune cells and transported to the lymphatic channel 92 where they are cleared from the tissue. The method 300 can be repeated as indicated by process block 314 until a sufficient number of sub-particles of the targeted tissue are cleared from the tissue to remove the targeted tissue or a portion thereof.

It should be appreciated that the method 300 is "color blind" to the color of the targeted tissue, because the ultrasound energy is not absorbed in a resonant process, such as light absorption.

In certain aspects, the systems and methods described herein can be applied to systems where the acoustic impedance of the targeted tissue 90 and the tissue 80 are different. The acoustic impedance of the targeted tissue 90 can be at least 10% greater than the acoustic impedance of the tissue 80, including but not limited to, at least 25% greater, at least 50% greater, at least 75% greater, at least 100% greater, at least 200% greater, at least 500% greater, or the acoustic impedance of the targeted tissue 90 can be at least 1000% greater than the acoustic impedance of the tissue 80. The acoustic impedance of the targeted tissue 90 can be less than the acoustic impedance of the tissue 80. The acoustic impedance of an object or medium is typically reported in rayls and can be calculated for any object or medium ($Z=\rho V$, where $\rho$ is the density of the object or medium and $V$ is the acoustic velocity in the object or medium).

In certain aspects, the tissue 80 can have an acoustic impedance between 1.3 MRayls and 2.0 MRayls, including but not limited to, an acoustic impedance between 1.5 MRayls and 1.8 MRayls, or an acoustic impedance between 1.6 MRayls and 1.7 MRayls.

In certain aspects, the targeted tissue 90 can have an acoustic impedance between 2 MRayls and 10 MRayls, including but not limited to an acoustic impedance between 2 MRayls and 5 MRayls. In certain aspects, the targeted tissue 90 can have an acoustic impedance less than the acoustic impedance of the tissue 80, such as an acoustic impedance of about 1.4 MRayls.

The systems and methods described herein can include and/or utilize a database of acoustic impedances relating to the various targeted tissues 90 and tissues 80 described herein.

The systems and methods described herein can be utilized for the treatment of cellulite. For example, the acoustic impedance of the fibrous septae, which hold pockets of fat, is greater than the acoustic impedance of the surrounding fat. The acoustic energy can be directed to a boundary between the fibrous septae and the fat to fragment a portion of the fibrous septae. This can result in release of skin above the fat, thereby smoothing the skin above the fat. If the acoustic energy is misaimed and directed to only the fat, the acoustic energy does not damage the fat layer, because the acoustic energy was configured to impact the boundary. Such methods can further include steps to treat the far, for example, methods described in U.S. Pat. Nos. 8,133,180 and 8,663,112, which are hereby incorporated in their entirety by reference.

The control system 104 can be configured to receive a user input, such as an input that identifies the targeted tissue 90 or the acoustic impedance of the targeted tissue 90. The control system 104 can then automatically calculate the acoustic energy necessary to achieve the desired effect and can be configured to direct the ultrasound energy source 102 to deliver the propagating ultrasound energy 108 having the calculated properties.

The systems and methods disclosed herein can be useful for medical and non-medical applications. In one aspect, the systems and methods disclosed herein can be useful for acoustic tissue treatment. In one aspect, the systems and methods disclosed herein can be useful for cosmetic applications, such as the cosmetic enhancement of skin, subcutaneous tissue layers, or a combination thereof. The systems and methods disclosed herein can be useful for non-invasive and/or non-surgical applications.

The present invention has been described above with reference to various exemplary configurations. However, those skilled in the art will recognize that changes and modifications may be made to the exemplary configurations without departing from the scope of the present invention. For example, the various operational steps, as well as the components for carrying out the operational steps, may be implemented in alternate ways depending upon the particular application or in consideration of any number of cost functions associated with the operation of the system, e.g., various of the steps may be deleted, modified, or combined with other steps. Further, it should be noted that while the method and system for ultrasound treatment as described above is suitable for use by a user proximate the patient, the system can also be accessed remotely, i.e., the user can view through a remote display having imaging information transmitted in various manners of communication, such as by satellite/wireless or by wired connections such as IP or digital cable networks and the like, and can direct a local practitioner as to the suitable placement for the transducer. Moreover, while the various exemplary embodiments may comprise non-invasive configurations, system can also be configured for at least some level of invasive treatment application. These and other changes or modifications are intended to be included within the scope of the present invention, as set forth in the following claims.

I claim:

1. A non-invasive method of removing a targeted tissue from tissue, the targeted tissue having an acoustic impedance mismatch with the tissue, the method comprising:
   a) targeting the targeted tissue;
   b) coupling an ultrasound energy source to the targeted tissue, the ultrasound energy source configured to produce a pulsed first ultrasound energy having a frequency of between 100kHz and 200 MHZ, a pulse duration of between 1 ps and 1 ms, and a power between 1 kW and 50 kW;
   c) initiating an acousto-mechanical or acousto-elastic effect in the targeted tissue by directing from 500 nJ to 5 J of the pulsed first ultrasound energy from the ultrasound energy source into the targeted tissue.

2. The method of claim 1, wherein the pulse duration is between 1 ns and 10 µs.

3. The method of claim 1, wherein the frequency is between 1 MHz and 30 MHz.

4. The method of claim 1, the method further comprising:
   d) subsequent to step c), directing a second ultrasound energy from the ultrasound energy source or a second ultrasound energy source having an ultrasound pulse duration of at least 100 µs into the targeted tissue or a portion thereof, thereby initiating a second effect in the targeted tissue or the portion thereof.

5. The method of claim 4, wherein the second effect is a cavitation effect or a thermal effect.

6. The method of claim 1, wherein the acousto-mechanical or acousto-elastic effect exceeds a fragmentation threshold of the targeted tissue.

7. The method of claim 1, wherein the pulsed first ultrasound energy is a single ultrasound pulse.

8. The method of claim 1, wherein the tissue is subcutaneous tissue.

9. The method of claim 1, wherein the acousto-mechanical or acousto-elastic effect moves at least a portion of the targeted tissue in the tissue.

10. The method of claim 9, wherein the acousto-mechanical or acousto-elastic effect moves at least a portion of the targeted tissue toward a surface of the tissue.

11. The method of claim 10, wherein the acousto-mechanical or acousto-elastic effect expels at least a portion of the targeted tissue from the tissue.

12. The method of claim 9, wherein the acousto-mechanical or acousto-elastic effect moves at least a portion of the targeted tissue away from a surface of the tissue.

13. The method of claim 12, wherein the acousto-mechanical or acousto-elastic effect moves at least a portion of the targeted tissue to a depth where they are no longer visible through an epidermis.

14. An ultrasound treatment system for targeted tissue removal comprising:
- an ultrasound energy source configured to emit a propagating ultrasound energy having a propagating ultrasound pulse duration between 100 ps and 1 ms, a propagating ultrasound pulse power ranging from 1 kW to 50 kW, and a propagating ultrasound frequency between 100 kHz and 200 MHz;
- a control system configured to initiate an acousto-mechanical or acousto-elastic effect within a targeted tissue located in a target zone within a medium by directing the ultrasound energy source to emit the propagating ultrasound energy to the targeted tissue at an intensity gain between 500 and 25,000, thereby initiating an acousto-mechanical or acousto-elastic effect within the targeted tissue.

15. The system of claim 14, wherein the propagating ultrasound pulse duration is between 1 ns and 10 μs.

16. The system of claim 14, wherein the propagating ultrasound frequency is between 1 MHz and 30 MHz.

17. The system of claim 14, the system optionally comprising a second ultrasound energy source, wherein the ultrasound energy source or the second ultrasound energy source is configured to emit a second propagating ultrasound energy having a second propagating ultrasound pulse duration of at least 100 μs, the control system configured to direct the ultrasound energy source or the second ultrasound energy source to emit the second propagating ultrasound energy to the target zone.

18. The system of claim 14, wherein the ultrasound energy source is configured to emit a single ultrasound pulse, the single ultrasound pulse initiating the acousto-mechanical or acousto-elastic effect within the targeted tissue.

* * * * *

UNITED STATES PATENT AND TRADEMARK OFFICE
CERTIFICATE OF CORRECTION

| | | |
|---|---|---|
| PATENT NO. | : 12,239,854 B2 | Page 1 of 1 |
| APPLICATION NO. | : 17/232404 | |
| DATED | : March 4, 2025 | |
| INVENTOR(S) | : Michael H. Slayton | |

It is certified that error appears in the above-identified patent and that said Letters Patent is hereby corrected as shown below:

In the Specification

In Column 5, Line 23, delete "us" and insert --µs-- therefor

In Column 5, Line 23, delete "us" and insert --µs-- therefor

In Column 6, Line 20, delete "us" and insert --µs-- therefor

In Column 6, Line 35, delete "us" and insert --µs-- therefor

In Column 6, Line 35, delete "us" and insert --µs-- therefor

In Column 6, Line 36, delete "us" and insert --µs-- therefor

In Column 6, Line 36, delete "us" and insert --µs-- therefor

In Column 10, Line 61, delete "us" and insert --µs-- therefor

In the Claims

In Column 14, Line 32, in Claim 1, delete "MHZ," and insert --MHz,-- therefor

Signed and Sealed this
Seventeenth Day of June, 2025

Coke Morgan Stewart
*Acting Director of the United States Patent and Trademark Office*